Sept. 20, 1960 R. V. LINDQUIST Plant Pat. 1,971
ROSE PLANT
Filed Jan. 12, 1960 2 Sheets-Sheet 1
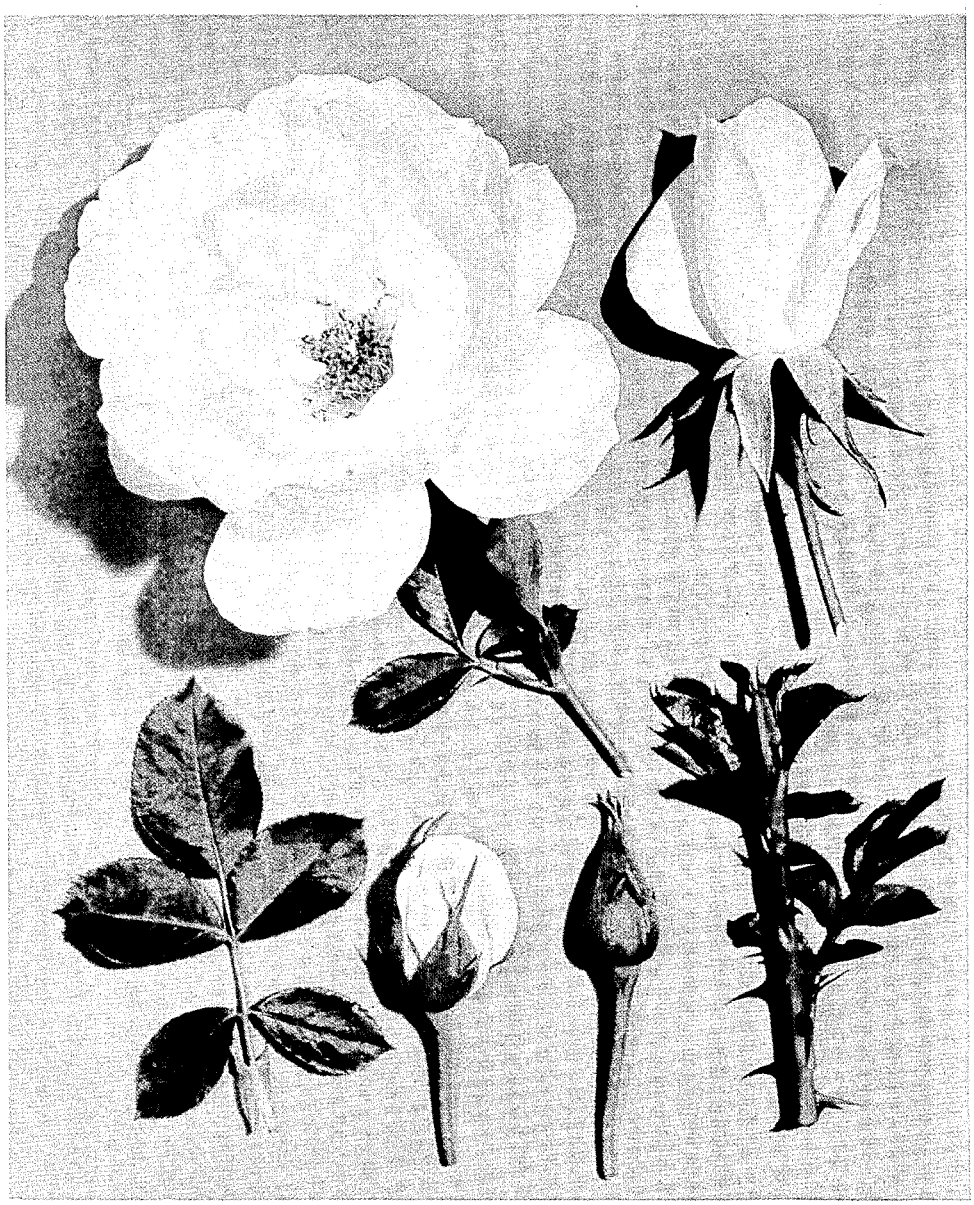
Inventor.
R. V. Lindquist
By: Robb & Robb
Attorneys.

Sept. 20, 1960 R. V. LINDQUIST Plant Pat. 1,971
ROSE PLANT
Filed Jan. 12, 1960 2 Sheets-Sheet 2
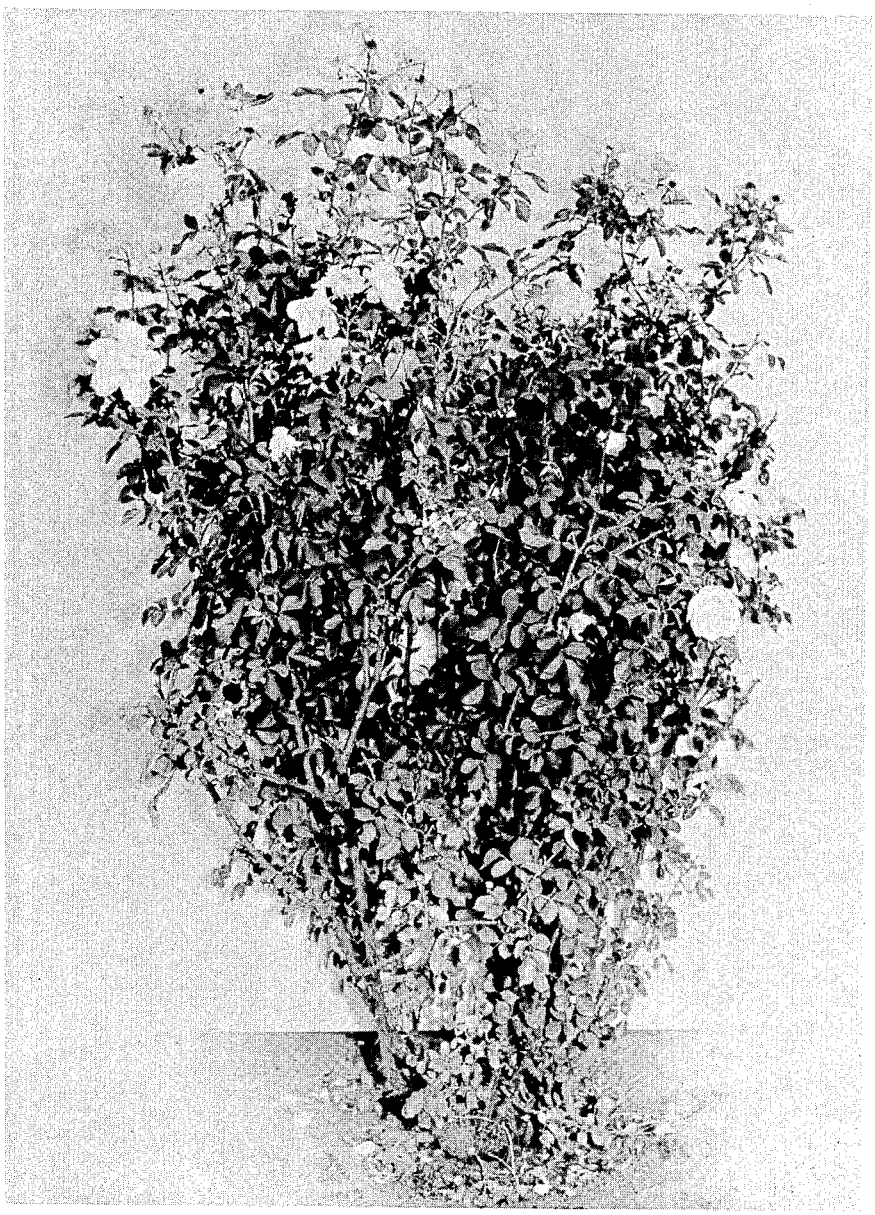
INVENTOR
R. V. Lindquist
BY Robb & Robb
ATTORNEYS United States Patent Office Plant Pat. 1,971
Patented Sept. 20, 1960

1,971

ROSE PLANT

Robert V. Lindquist, Hemet, Calif., assignor to Hemet Wholesale, Hemet, Calif., a partnership Filed Jan. 12, 1960, Ser. No. 2,087

1 Claim. (Cl. 47—61)

The present invention relates to a new and distinct variety of rose plant of the hybrid grandiflora class, which was originated by me by crossing the variety "Joanna Hill" (unpatented) with an unnamed and unpatented seedling.

As the result of this breeding, I have produced a new rose variety which is particularly characterized as to novelty by a unique combination of outstanding characteristics which distinguish it from its parents, as well as from all other varieties of which I am aware, such characteristics including a vigorous and upright habit of plant growth, and an unusually heavy production of blooms of near white color.

Asexual reproduction of my new variety by budding, as performed at Hemet, California, shows that the foregoing characteristics and distinctions come true to form and are established and transmitted through succeeding propagations.

The accompanying drawings show typical specimens of the vegetative growth and flowers of my new variety in different stages of development and as depicted in color as nearly true as it is reasonably possible to make the same in a color illustration of this character, as well as a view of a typical complete plant, as depicted in black-and-white, to show the outstanding plant habits.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated:

Type: Half-hardy; tall; bush; for cut flowers and for garden decoration.
Class: Hybrid grandiflora.
Breeding: Seedling.
*Seed parent.*—"Joanna Hill."
*Pollen parent.*—An unnamed seedling.
Propagation: Holds its distinguishing characteristics through succeeding propagations by budding.

*Flower*

Locality where grown and observed: Hemet, California.
Flowers borne: Sometimes singly, but usually from 3 to 5 or more to stem; in irregular clusters; on stems of normal strength and medium length.
Quantity of bloom: Free, outdoors.
Continuity: Continuous during growing season.
Fragrance: Slight. Nature—tea.
Bud:
*Peduncle.*—Average length; average caliper; erect; moderately smooth; few gland-tipped cilia; few hairs. Color—near Elm Green, Plate XVII (Ridgway), with shadings of Brick Red, Plate XIII (Ridgway).
*Before calyx breaks.*—Size—medium. Form—medium length; somewhat pointed; with foliaceous appendages; few gland-tipped cilia on the surface of the bud; usually with slender foliaceous parts extending beyond the tip of the bud equal to ¼ or more of its length.

*As calyx breaks.*—Color—base near Naples Yellow, Plate 403/2, page 121 (Wilson), shading to near white at outer edge of petals.
*Sepals.*—Inner surface—with fine, woolly tomentum. Margins—with foliaceous appendages and gland-tipped cilia.
*As first petal opens.*—Size—average. Form—medium length; pointed. Color: outside—base near Naples Yellow, Plate 403/2, page 121 (Wilson), shading to near white at outer edge of petals; inside—near Naples Yellow, Plate 403/2, page 121 (Wilson) at base, shading to near white at outer edge of petals.
*Opening.*—Opens up well; is not retarded from opening by cold, hot, wet or dry weather.

Bloom:
*Size (when fully open).*—From 3 inches to 5 inches.
*Petalage.*—Semi-double; from 15 to 25 petals, plus from 3 to 5 petaloids; arranged regularly.
*Form.*—High-centered at first, but becoming open-cupped; petals at first remaining somewhat cupped; with tips reflexed and rolled inward, but later becoming somewhat loosely cupped at maturity, with tips rolled inward.

Petals:
*Texture.*—Medium thin; soft. Inside—slightly satiny. Outside—slightly satiny.
*Shape.*—Outside—oval, with occasional petal scalloped, and with apex rounded and having 1 or 2 notches. Intermediate—oval, with apex rounded. Inside—nearly oval, with apex rounded.

This description of a newly opened flower was made from a rose grown outdoors in the month of October at Hemet, California:

*Color.*—Outer petal: outside surface—base near Naples Yellow, Plate 403/2, page 121 (Wilson), shading to near white at outer edge of petals; inside surface—base near Naples Yellow, plate 403/2, page 121 (Wilson), shading to near white at outer edge of petals. Intermediate petal: outside surface—base near Naples Yellow, Plate 403/2, page 121 (Wilson), shading to near white at outer edge of petals; inside surface—base near Naples Yellow, Plate 403/2, page 121 (Wilson), shading to near white at outer edge of petals. Inner petal: outside surface—base near Naples Yellow, Plate 403/2, page 121 (Wilson), shading to near white at outer edge of petals; inside surface—base near Naples Yellow, Plate 403/2, page 121 (Wilson), shading to near white at outer edge of petals.

This description was made from a rose that was open for 3 days outdoors in the month of October at Hemet, California:

*Color.*—Outer petal: outside surface—base near Naples Yellow, Plate 403/2, page 121 (Wilson), shading to near white at outer edge of petals; inside surface—base near Naples Yellow, Plate 403/2, page 121 (Wilson), shading to near white at outer edge of petals. Inner petal: outside surface—base near Naples Yellow, Plate 403/2, page 121 (Wilson), shading to near white at outer edge of petals; inside surface—base near Naples Yellow, Plate 403/2, page 121 (Wilson), shading to near white at outer edge of petals.
*General color effect.*—Newly opened flower—near Naples Yellow, Plate 403/2, page 121 (Wilson), shading to near white at outer edge of petals. 3-days open—near Naples Yellow, Plate 403/2, page 121 (Wilson), shading to near white at outer edge of petals.

*Behavior.*—Drop off cleanly except for petaloids.

*Flower longevity.*—On bush in garden—3 or 4 days in October. Cut roses grown outdoors and kept at livingroom temperatures—3 or 4 days in October.

*Reproductive organs*

Stamens: Average number; arranged somewhat irregularly about pistils.

Filaments: From medium length to long; most with anthers. Color—base from near Tyrian Rose, Plate 24/2, page 24 (Wilson) to near Chrome Yellow, Plate 605/2, page 144 (Wilson).

Anthers: Medium size; all open approximately at once. Color: upper side—near Amber Yellow, Plate 505/1, page 132 (Wilson); under side—near Amber Yellow, Plate 505/2, page 132 (Wilson).

Pollen: Somewhat abundant. Color—near Nasturtium Orange, Plate 610/1, page 145 (Wilson).

Pistils: Many; from approximately 100 to 150 in number.

Styles: Moderately uneven; average length; average caliper; somewhat bunched. Color—near pale Dull Green Yellow, Plate XVII (Ridgway).

Stigma: Color—near Rose Opal, Plate 022/1, page 110 (Wilson).

Ovaries: Usually most enclosed in calyx but some protruding therefrom.

Hips: Average length; globular; with inconspicuous neck; moderately smooth; walls moderately thin. Color—near Zinc Orange, Plate XV (Ridgway), with shadings of near Rainette Green, Plate XXXI (Ridgway).

Sepals: Falling soon; medium length; spear-shaped. Color: inside—near light Fluorite Green, Plate XXXII (Ridgway); outside—near Biscay Green, Plate XVII (Ridgway).

Seeds: Average number (from 4 to 12); medium size.

*Plant*

Foliage:

*Leaves.*—Compound of usually 3 to 7 leaflets; normal abundance; medium size; somewhat leathery; semi-glossy.

*Leaflets.*—Shape—from oval to obovate, with apex sometimes obtuse and sometimes acute. Base—obtuse. Margin—serrate.

*Color.*—Mature: upper surface—near Empire Green, Plate XXXII (Ridgway); under surface—near Bice Green, Plate XVII (Ridgway). Young: upper surface—near Empire Green, Plate XXXII (Ridgway); under surface—near Dark Corinthian Purple, Plate XXXVIII (Ridgway).

*Rachis (the supporting stem of the compound leaf).*—Average size. Upper side—grooved, with few stipitate glands on edges. Under side—moderately prickly, with few stipitate glands.

*Stipules.*—Medium length; medium width; with short to medium length points turning out at an angle of about 45°.

*Disease resistance.*—Mildly resistant to mildew, as determined by comparison with other varieties grown under comparable cultural conditions at Hemet, California.

Growth:

*Habit.*—Upright; much-branched.

*Growth.*—Very vigorous.

*Canes.*—Medium caliper.

*Main stems.*—Color—near Bice Green, Plate XVII (Ridgway). Large prickles—several; from medium length to long; hooked downward; with moderately narrow base of medium length; color—near Cinnamon Brown, Plate XV (Ridgway). Small prickles—none. Hairs—none.

*Branches.*—Color—near Bice Green, Plate XVII (Ridgway). Large prickles—several; from medium length to long; hooked downward; with moderately narrow base of medium length; color—near Cinnamon Brown, Plate XV (Ridgway). Small prickles—none. Hairs—none.

*New shoots.*—Color—near Empire Green, Plate XXXII (Ridgway), with shadings of near Corinthian Purple, Plate XXXVIII (Ridgway). Large prickles—several; medium length; hooked downward; with moderately narrow base; color—near Dark Corinthian Purple, Plate XXXVIII (Ridgway). Small prickles—none. Hairs—none.

I claim:

A new and distinct variety of rose plant of the hybrid grandiflora class, substantially as herein shown and described, characterized particularly as to novelty by the unique combination of an upright and vigorous habit of plant growth, and heavy production of blooms of near white color.

No references cited.